United States Patent [19]

Biedermann

[11] 4,143,659
[45] Mar. 13, 1979

[54] STILLIGOUT OR DROPPER PARTICULARLY FOR INFUSION APPARATUS

[76] Inventor: Helmut Biedermann, Erzherzog-Eugenstrasse 19, Innsbruck, Austria, A-6020

[21] Appl. No.: 717,692

[22] Filed: Aug. 25, 1976

[30] Foreign Application Priority Data

Aug. 28, 1975 [AT] Austria ............................. 6639/75
Apr. 24, 1976 [AT] Austria ............................. 3795/76

[51] Int. Cl.² .......................................... A61M 05/16
[52] U.S. Cl. .......................... 128/214 C; 141/113; 222/420
[58] Field of Search ........... 128/213, 214 R, 214 C, 128/214.2, 227; 222/420; 141/113, 319

[56] References Cited

U.S. PATENT DOCUMENTS

| | | | |
|---|---|---|---|
| 2,675,000 | 4/1954 | Ford | 128/214 C |
| 2,729,212 | 1/1956 | Butler | 128/214 C |
| 2,844,147 | 7/1958 | Beacham | 128/214 C |
| 3,521,635 | 7/1970 | Koehn | 128/214 C |
| 3,744,492 | 7/1973 | Leibinsohn | 128/214 C |
| 3,941,126 | 3/1976 | Dietrich et al. | 128/214 C |

*Primary Examiner*—Dalton L. Truluck
*Attorney, Agent, or Firm*—McGlew and Tuttle

[57] ABSTRACT

A dropper for infusion liquid particularly for connecting an infusion bag to a catheter comprising a dropper housing defining an interior dropper chamber having an inlet connected at the top of the dropper chamber and an outlet tube extending into the chamber on a side opposite from the inlet. A deaeration opening is provided in association with the outlet tube for venting the interior of the chamber when the chamber is inverted into a filling position. The deaeration opening is positioned within the chamber at a level sufficient to define a first air volume bounded by a plane tangent to the deaeration opening and a portion of the dropper chamber above the plane, which volume is smaller than the remaining volume of the dropper chamber. A second volume is defined by a plane tangent to an opening of the inlet within the dropper chamber and a portion of the dropper chamber above the opening. The opening of the inlet is positioned so that the second volume is smaller than the first volume defined by the deaeration opening. When the dropper chamber is returned to an upright position after having been filled in an inverted position the difference between the first and second aforementioned volume provides a safety level of liquid above the outlet tube within the dropper chamber.

27 Claims, 11 Drawing Figures

STILLIGOUT OR DROPPER PARTICULARLY FOR INFUSION APPARATUS

The invention relates to a stilligout or dropper for infusion apparatus, particularly for connecting a tube from an infusion container to a tube leading to a catheter or the like.

Various types of stilligouts or droppers are known at the present time. They are mainly intended for infusion systems which function according to the gravity principle and best results have been obtained on bedridden patients.

One important requirement is that of preventing the penetration of air or air bubbles into the infusion tube located on the catheter side, so as to prevent air embolisms from developing in the patient. To this end known systems employ valve devices in the outlet opening. While such valve devices render the product appreciably more expensive they do not prevent the penetration of small air bubbles. Another type of dropper attempts to prevent the penetration of air or air bubbles through the provision of narrow ducts for the infusion liquid, which ducts are intended to cause the air bubbles to burst.

These expedients also render the product more expensive, as more complicated structures are needed, as is also a high degree of accuracy required for their construction.

Also, stilligouts or droppers have had to fulfill a new requirement, particularly recently. Accident victims frequently require infusions during their transportation in ambulances, in helicopters or in other forms of transport. As it was found that the necessity of suspending the infusion container at a relatively great height was a hampering and disturbing influence, infusion bags have been developed which can be squeezed by means of presser sleeves, and whose efficiency is not dependent on their position.

In order to exploit this advantage, it is thus necessary that the stilligout or dropper shall, independently of its position, permit the infusion liquid to be discharged from the stilligout or dropper free of air bubbles.

SUMMARY OF THE INVENTION

A stilligout or dropper which satisfies this requirement in a large measure comprises an outlet tube which extends over the volumetric centre of the dropper container or housing. When the dropper is being filled, the infusion liquid level rises to the outlet opening, the latter serving as a de-aeration opening, and then flows into the infusion tube. It is ensured, through the choice of a smaller volume for the drop chamber, that (even when the dropper is tilted), the liquid level will always cover off the outlet opening. However, it can occur, particularly when there is vibration and in the drip position, that air penetrates into the infusion tube, and the liquid level covers off the outlet opening, that is only liquid flows over into the outlet opening.

Accordingly, an object of the invention is to provide a dropper or stilligout which can function efficiently and reliably independently of its position, and which enables the abovementioned drawbacks to be eliminated, and which, at least in its preferred embodiments, can be manufactured at reasonable cost.

According to the invention, the volume located on the wall side of a de-aeration opening is at most equal to each of the two part-volumes, which are intersected by a plane lying tangent to the outlet opening and the volume lying on the wall side of the de-aeration opening is greater than the volume located on the wall side of the inlet opening.

The greatest advantages of the invention are particularly realised in use with a pressure infusion system having an infusion bag surrounded by a presser sleeve. The dropper is filled in the following manner: the infusion bag is held with its outlet opening facing upwards and the dropper is also in a position in which its de-aeration opening assumes the highest position. The infusion bag is then subjected to pressure or a cutoff or clamp is opened. The air present in the infusion bag can escape, and the infusion liquid rises in the dropper as far as the de-aeration opening whereupon the infusion liquid can reach the infusion tube on the catheter side. The invention ensures that there will be a safety distance of the liquid level about the outlet opening in any position of the stilligout dropper, as a result of which any penetration of air into the infusion tube is precluded. Also, de-aeration of the infusion bag takes place so that the infusion bag may also lie in any position.

Advantageously the dropper is approximatey spherical. Conveniently, and in particular with a view to reducing the air volume needed for the drop counting, the dropper is provided with a domed protuberance, in which the inlet opening is formed.

In a preferred embodiment of the invention, the stilligout or dropper is resiliently deformable. The outlet tube may be pivotal. These expedients enable the air bubble volume to be regulated in a simple manner. Preferably, the de-aeration opening is formed on an outwardly opening de-aeration tube.

It may also be found advantageous if the de-aeration opening opens out into an outlet tube and is formed on a de-aeration tube provided with small plate extending in the flow direction. In another embodiment of the invention, the de-aeration opening is equipped with a closure plug or the like secured by an anchor which extends through the de-aeration tube.

In a stilligout or dropper according to the invention, which can be simply and efficiently handled, the de-aeration opening or de-aeration tube and/or the outlet opening or outlet tube is provided with a pressure relief valve. The pressure relief valve may be a one-way valve. In a stilligout or dropper according to the invention, which can be manufactured at reasonable cost, comprises a common outlet and de-aeration opening. Preferably, a displacement body, extending into the inside of the dropper, is arranged on the base or support of the outlet or de-aeration tube.

The invention is further described below by way of example with reference to the accompanying drawings, reference also being made to the de-aeration process. The de-aeration process is not to be interpreted in any restrictive sense.

DESCRIPTION OF THE PREFERRED EMBODIMENT

Figure 1:
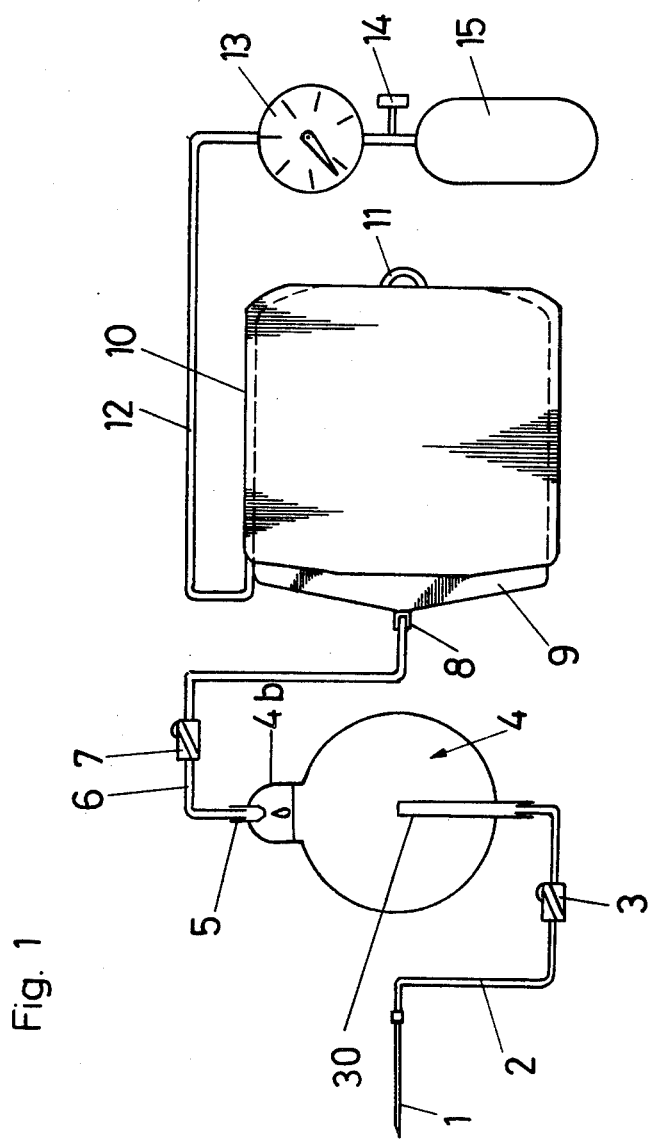
FIG. 1 is a schematic view of an infusion apparatus incorporating a stilligout or dropper according to the invention.

The apparatus shown in FIG. 1 comprises a stilligout or dropper 4 having an inlet or outlet tube 5 and an infusion bag 9 surrounded by a pneumatic presser sleeve 10. The pneumatic presser sleeve 10 communicates with a compressed air container 15 by way of a tube 12, a manometer 13 and a cutoff cock 14. An air pump may replace the compressed air container 15.

The infusion bag 9 communicates, by way of a hose 6, with the inlet 5 of the stilligout or dropper 4. The inlet 5 is constructed, inside the stilligout or dropper 4, as a drip nipple. The inlet 5 lies in a dome-shaped protuberance 4b of the stilligout or dropper. The hose 6 is provided with a roll clip or clamp 7. An outlet tube 30 of the dropper 4 communicates, by way of a hose 2 and a roll clip 3, with a vein catheter 1.

This outlet tube may be pivotally mounted on the dropper 4 to increase the ease of manipulation thereof.

As already mentioned the advantages of the stilligout or dropper according to the invention, are particularly apparent in the case of the rescue of injured persons by helicopter or on mountains; this is because, when the stilligout or dropper is correctly de-aerated, this stilligout or dropper can function efficiently irrespective of its instantaneous position, and the penetration of air and, hence, the danger of an air embolism are precluded.

Figure 2:
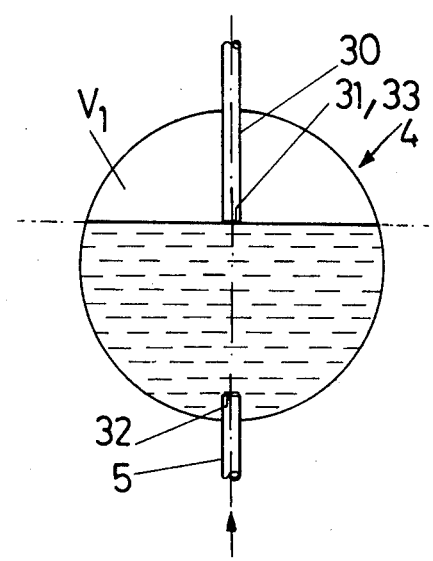
FIG. 2 illustrates the de-aeration of a stilligout or dropper according to the invention, the stilligout or dropper having a common outlet and de-aeration openings.
Figure 3:
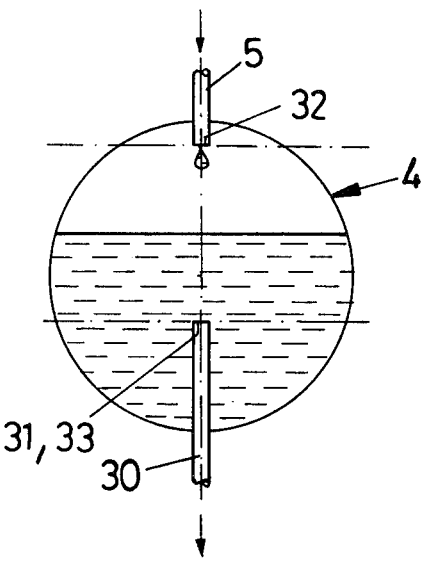
FIG. 3 illustrates the stilligout or dropper shown in FIG. 2, in the counting position.

FIGS. 2 and 3 illustrate another stilligout dropper 4. The dropper comprises a common outlet and de-aeration opening 31, 33. For effecting de-aeration, the common outlet and de-aeration opening 31, 33 is brought into its uppermost position and infusion liquid is introduced through the inlet opening 32. The infusion liquid rises while the dropper is being de-aerated, until the liquid level has reached the common outlet and de-aeration opening 31, 33, whereupon the infusion liquid rises further into the outlet tube 30.

The volume $V_1$, present on the wall side of the deaeration opening 31, determines the size of the air bubbles remaining in the stilligout or dropper.

In the main position of usage, shown in FIG. 3, the maximum safety distance exists between the liquid level and the outlet openin 31.

Figure 4:
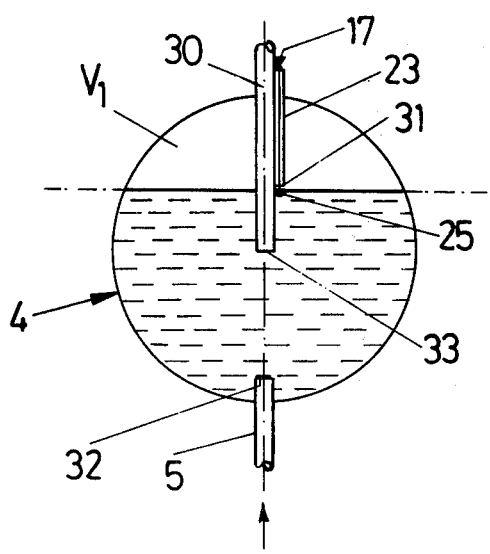
FIG. 4 illustrates a stilligout or dropper according to the invention, with its own de-aeration tube, the stilligout or dropper being shown de-aerated or filled.

FIG. 4 shows a stilligout or dropper, with its own de-aeration opening 31, in the filling position. The deaeration opening 31 lies on a de-aeration tube 23, which opens in the outward direction, and can be closed off with a plug 17, which is secured by an anchor 25. The outlet opening 33 lies at the centre of the spherical dropper 4.

To ensure that air cannot penetrate into the outlet tube 30 in any position of the dropper 4, the de-aeration opening 31 is so positioned that the volume $V_1$, located on the wall side of the opening 31, is greater than each of the two part-volumes which are cut by a plane lying tangential to the outlet opening 31. Further, with a view to forming an air bubble for counting drops, the volume lying on the wall side of the de-aeration opening 31 is larger than the volume lying on the wall side of the inlet opening 32, the difference between the two volumes corresponding to the utilisable air bubble volume.

Figure 5:
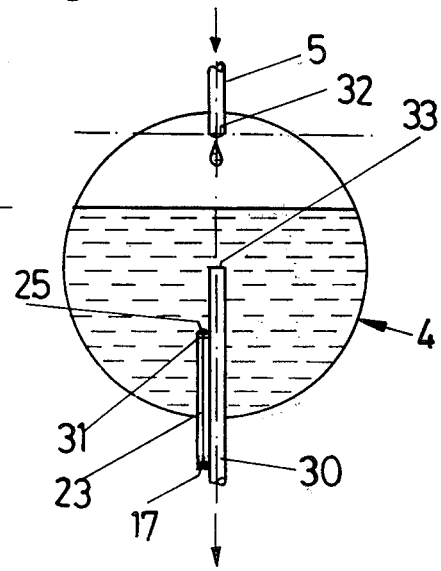
FIG. 5 illustrates the stilligout or dropper shown in FIG. 4, in the counting position.

The aforementioned volumes are defined by providing that the outlet opening 31, 33 in FIGS. 2 and 3, and the de-aeration opening 31 in FIGS. 4 and 5 are located at a point well within the chamber 4 and less than half the distance across the chamber in alignment with the inlet or inlet tube 5. It should also be noted that the inlet or inlet tube 5 has an inlet opening 32 which extends into the chamber 4 to a distance less than the outlet opening of FIGS. 2 and 3 and the de-aeration opening of FIGS. 4 and 5. Also as can be seen from the figures the outlet and/or de-aeration openings 31, 33 are disposed at the end of the outlet or de-aeration tubes 30 or 23 respectively.

Figure 6:
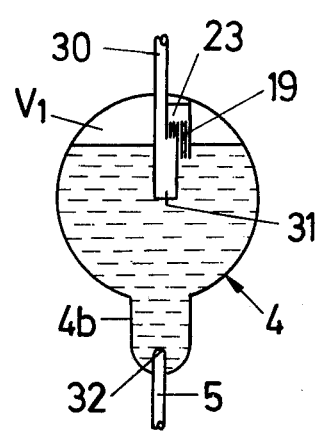
FIGS. 6 to 9 illustrate further stilligouts or droppers according to the invention.

The stilligout or dropper shown in FIG. 6 comprises a de-aeration tube 23 which opens into an outlet tube 30. The de-aeration tube 23 is provided, at the point where it opens into the outlet tube 30 with small plates 19 which extend in the flow direction, the plates 19 serving to prevent suction occurring in the vicinity of the inner opening of the de-aeration tube 23, so that the air bubble in the chamber cannot escape.

Figure 7:
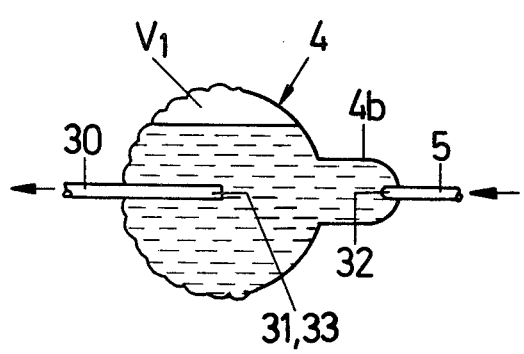

FIG. 7 shows a stilligout or dropper 4 which is resiliently deformable.

Figure 8:
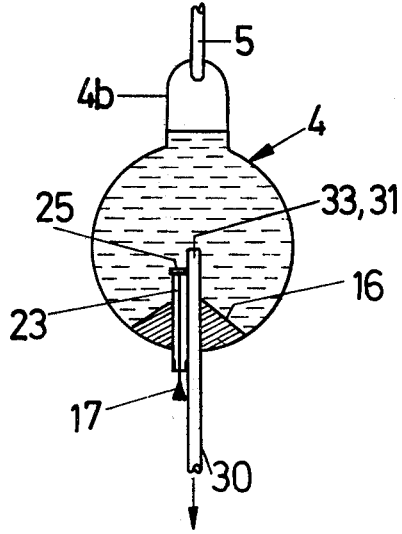
Figure 9:
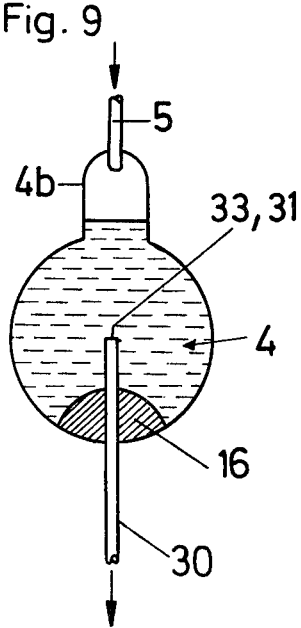

FIGS. 8 and 9 show stilligouts or droppers in which the air bubble in the dropper 4 can be made still smaller through the provision of a tapered displacement body 16 on the base or support of the outlet or de-aeration tube 30,23.

Figure 10:
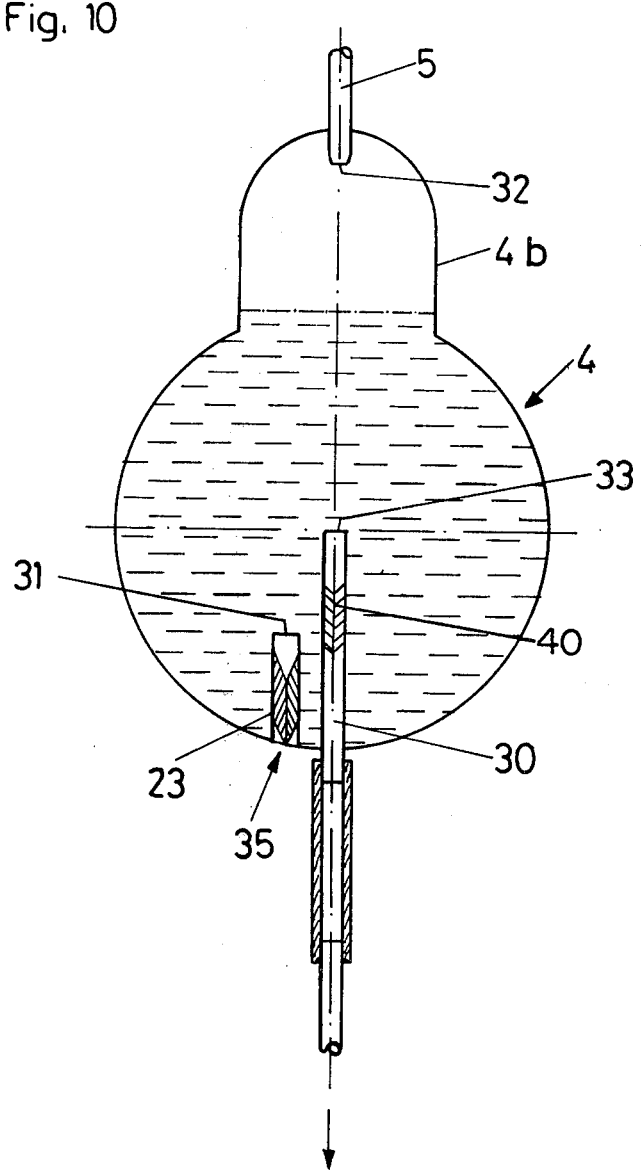
FIG. 10 illustrates a stilligout or dropper according to the invention, the stilligout or dropper having a dome-like protuberance and being provided with a pressure relief valve in the de-aeration duct.

FIG. 10 illustrates a stilligout or dropper having a de-aeration tube 23 provided with a pressure relief valve 35 in the form of two rubber lips. The presence of the pressure relief valve 35 affords a large number of advantages, one of which consists in the protection it gives to the patient. For example, if it becomes necessary for the catheter or the like to penetrate the vein wall, during an infusion carried out while the patient is being transported, then the pressurized infusion liquid builds up in the tissue or under the skin of the patient. A greater danger to the patient can be precluded by opening the valve 35 at an overpressure thereby allowing the infusion liquid to run off. A similar valve 40 may be provided on the tube 30 to vent fluid out of the chamber 4.

The use of a pressure relief valve in the outlet tube 30 is also feasible. This simplifies, in particular, the change-over of the infusion container 9 as, when the latter is removed, the liquid level in the stilligout dropper is maintained, and penetration of additional air is prevented from occurring. Also, possible backflow of blood is prevented when the pressure relief valve 35 is a one-way valve.

An advantageous de-aeration and filling process of an infusion system comprising a dropper 4 according to the invention will now be described.

Figure 11:
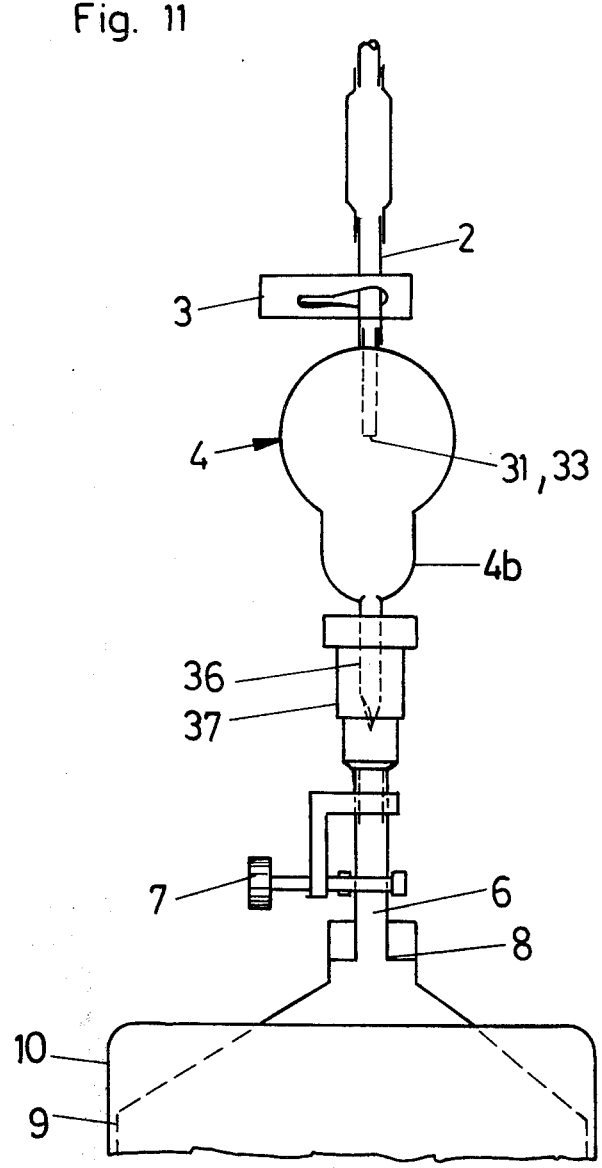
FIG. 11 is a schematic view showing a stilligout or dropper according to the invention and associated devices during de-aeration of the stilligout or dropper.

In the lowermost position in FIG. 11, the infusion bag 9 is surrounded by a presser sleeve 10, the opening of the bag 9 facing upwards. Continuing, in upward sequence (as viewed in FIG. 11), are: the hose 6, located on the container side and equipped with a clip or clamp 7; the dropper 4 in the filling position, the dropper being held, by way of a tapering tube 36 lying on the inlet side, in a connection piece 37; and, finally, the hose 2, which is located on the catheter side and is equipped with a further clip or clamp 3.

If the clips 7 and 3 are opened, any air which may be present escapes from the infusion bag 9, whereupon the infusion liquid rises to the de-aeration opening 31 in the dropper, and then fills the hose 2 lying on the catheter side.

After the de-aeration and filling process, the infusion system is capable of reliable operation in any position, and air will be unable to penetrate into the hose located on the catheter side. For enabling the infusion bag 9 to be replaced, it is advantageous to provide the tapered tube 36, located on the inlet side, of the dropper with a longitudinal notch or recess in part of its tip. This enables de-aeration to be carried out without altering the level of liquid in the dropper 4. This takes place by only pushing the tapered tube 36 into the connecting piece 37 up to the notched area of tube 36, whereupon the air can escape through the notch or recess. After de-aeration, the tapered tube 36 is pushed in to the full extent and sealed off.

Naturally, the dropper 4 according to the invention may, conveniently, be used with infusion flasks (which are widely used) on stands, that is to say in accordance with the gravity infusion principle.

The main advantages of the invention may, however, be summarised in the following way:

Infusion therapy based on the gravity principle or pressure infusion may be carried out and the infusion therapy is independent of position, except for intermittent flow measurement, the use of an infusion stand or support being dispensed with and the occurrence of air embolisms by the pressure mechanism being prevented.

The high pressure, realised by the pneumatic system, remains, in the infusion system, restricted to the bag and to a short part (up to the roll clip 7) of the hose attached to it, as the result of which there is only a very small risk of unsealed places, and it becomes possible to replace bags which are filled, and which are even under pressure. Optimal fixing or attachment of the frequently precious vein cannulas is rendered possible. It also becomes possible to secure the attachment to the hose system, as this attachment has to remain for the duration of the infusion therapy, and cannot be discontinued.

The infusion bag and equipment can be directly fixed on or in the patient's clothing, as a result of which changes in position of the patient are facilitated, the infusion therapy is not interrupted, and the vein cannulas are maintained in a condition of efficient operation.

The infusion solutions are not exposed to cold.

The patient can be, and remain, warmly wrapped up (e.g. in a sleeping bag), even when the bags are being changed or during flow checks, as manipulation only has to take place in the vicinities of the pneumatic system of the bag, of the stilligout or dropper, and at the discharge hose system 2 as far as the roll clip 3.

If the pneumatic system is out of use, infusion can be continued by gravity, that is to say simply by suspending the bag. If necessary, volume can be substituted intravenously very rapidly in consequence of the high pressure, but infusion can also be carried out intra-arterially (e.g. in the case of severe shock conditions). There is only small risk of importation of germs into the system, as coupling-over takes place, during bag replacement, at the connection with the stilligout or dropper, and there can be no contact with the skin of the patient, who is often restless. The technological requirements for the system are minimal. Continuous injection of medicaments can take place, particularly when a rubber connector is used for the hose on the catheter side.

Various modifications may be made within the scope of the invention. For example a wide variety of shapes of shiftable outlet tubes, and de-aeration tubes and the like may be used.

What I claim is:

1. A drip chamber for determining the rate of flow of a liquid comprising, a dropper housing defining an interior dropper chamber, an inlet tube connected into the top of said dropper chamber, an outlet tube extending well into said chamber on an opposite side of said inlet tube to a point less than half the distance across said chamber on an axis aligned with said inlet tube, said outlet tube having an outlet opening at an end within said chamber for venting the air and exiting the liquid of said interior chamber, said inlet tube extending into said chamber to a distance less than said outlet tube, said chamber being fillable upon inverting said dropper housing, the liquid fed through said inlet tube up to said outlet opening, the liquid surface and a portion of said chamber defining a first volume of air, said first volume being smaller than each further volume defined by a liquid surface tangent to said outlet opening and a remaining portion of said chamber in any other orientation of the dropper housing, said first volume being larger than the smallest volume defined by a liquid surface which tangents the inlet opening and a remaining portion of said chamber, so when the dropper housing is placed back in an upright position after filling, the liquid surface is at a safety level above the outlet opening.

2. A drip chamber as in claim 1, wherein a displacement body is arranged on the base of the outlet tube and wherein said first volume of air is reduced in the inverted orientation of said dropper housing for providing a larger safety level above said outlet opening.

3. A drip chamber as in claim 1, including a pressure relief valve in said outlet tube.

4. A drip chamber as claimed in claim 3, wherein said pressure relief valve comprises a one way valve.

5. A drip chamber for determining the rate of flow of a liquid comprising a dropper housing defining an interior dropper chamber, an inlet connected into the top of said chamber, an outlet tube extending into said chamber on an opposite side of said housing from said inlet, having an outlet opening at its end within said chamber for exiting said liquid and a separate de-aeration opening for venting the air out of the interior of said chamber, said de-aeration opening being located at a point well within said chamber and less than half the distance across said chamber in alignment with said inlet, said chamber being fillable upon inverting said dropper housing, said liquid fed through said inlet up to said de-aeration opening, said inlet extending into said chamber to a distance less than said de-aeration opening, said liquid surface with said chamber defining a first volume of air, said first volume being smaller than the smallest volume which is defined by a liquid surface tangenting the outlet opening and said chamber and said first volume being larger than the smallest volume being defined by a liquid surface tangenting the inlet opening and said chamber, the liquid surface being at a safety level above the outlet opening in all orientations of the dropper housing.

6. A drip chamber as in claim 5, wherein said de-aeration opening is provided on a separate tube which opens out into the outlet tube, said separate tube having a greater resistance to flow than said outlet opening.

7. A drip chamber as in claim 5, wherein said de-aeration opening is provided on a separate tube and said separate tube is provided with small plates which extend in the flow direction.

8. A drip chamber as in claim 5, wherein said de-aeration opening is provided on a separate tube, said separate tube opening outside said chamber.

9. A drip chamber as in claim 8, said separate tube having a closure plug.

10. A drip chamber as in claim 5, wherein said de-aeration opening is provided on a separate tube and including a pressure relief valve in said separate tube.

11. A drip chamber as in claim 10, wherein said pressure relief valve comprises a one way valve.

12. A drip chamber as in claim 5, including a pressure relief valve in said outlet tube.

13. A drip chamber as claimed in claim 5, wherein said dropper housing includes a main spherical portion and a separate bulbous portion of a smaller diameter than said spherical portion extending upwardly therefrom, said inlet extending into the top of said bulbous portion, said bulbous portion having a volume which is equal to said volume of air and said outlet tube extending into said spherical portion.

14. A dropper for fusion liquids particularly for connecting an infusion bag to a catheter, comprising a dropper housing defining an interior dropper chamber, an inlet connected into the top of said dropper chamber, an outlet tube extending into said chamber on a side thereof which is opposite to said inlet, and de-aeration means associated with said outlet tube for venting the interior of said chamber and having an interior opening located well within said chamber at an end of said de-aeration means spaced inwardly from the side having said outlet tube and less than half the distance across said chamber in alignment with said inlet, said inlet extending into said chamber to a distance less than said interior opening, said chamber being fillable with liquid upon inverting said dropper housing and filling the chamber with liquid through said inlet, said de-aeration means interior opening being spaced from said outlet opening within said chamber and also being spaced from its associated wall, a plane tangent to said de-aeration means interior opening defining a first liquid volume so that the filling does not proceed beyond the interior opening and the remaining space in said chamber remains full of air and defines a second air volume which is smaller than said first liquid volume, so that the air always remains below said inlet when the dropper housing is placed back in an upright position and the liquid level always remains above the interior opening of said de-aeration means.

15. A dropper according to claim 14, wherein said outlet tube is pivotal.

16. A stilligout or dropper according to claim 14, including a displacement body which extends into said inside of the dropper housing.

17. A dropper according to claim 14, wherein said de-aeration means comprises said outlet tube, said outlet tube extending inwardly from the associated side toward said inlet.

18. A dropper according to claim 14, wherein said de-aeration means comprises a separate tube, said outlet tube being arranged alongside said separate tube and said separate tube defining said interior opening and said outlet tube defining a separate outlet tube opening inside said chamber.

19. A dropper according to claim 18, wherein said separate tube interior opening extends into said chamber to a distance spaced from the associated wall of said outlet tube but by an amount which is less than the amount in which said outlet tube extends into said chamber.

20. A dropper according to claim 14, including displacement means in said chamber extending upwardly from the side containing said outlet tube and reducing the volume at the interior of said chamber.

21. A dropper according to claim 14, wherein said de-aeration means interior opening is formed by a separate de-aeration tube having a plurality of plate members arranged in spaced location which extend in the flow direction.

22. A dropper according to claim 14, wherein said de-aeration means comprises a separate tube having a closure plug and an anchor connected to said plug for moving said plug.

23. A dropper according to claim 14, including a pressure relief valve in said outlet tube.

24. A dropper according to claim 23, wherein said pressure relief valve comprises a oneway valve.

25. A dropper for fusion liquids particularly for connecting an infusion bag to a catheter, comprising a dropper housing defining an interior dropper chamber, an inlet connected into the top of said dropper chamber, an outlet tube extending into said chamber on a side thereof which is opposite to said inlet, and de-aeration means associated with said outlet tube for venting the interior of said chamber and having an interior opening at one end located well within said chamber to a point less than half the distance across said chamber in alignment with said inlet spaced inwardly from the side having said outlet tube, said inlet extending into said chamber to a distance less than said interior opening, said chamber being fillable with liquid upon inverting said dropper housing and filling the chamber with liquid through said inlet, said de-aeration means interior opening being spaced from said outlet within said chamber and also being spaced from its associated wall so that filling does not proceed beyond the interior opening and the remaining space in said chamber remains full of air, so that the air always remains below said inlet when the bottle is placed back in an upright position and the liquid level always remains above the interior of said de-aeration means, wherein said de-aeration means comprises a separate tube, said outlet tube being arranged alongside said separate tube and said separate tube defining said interior opening and said outlet tube defining a separate outlet tube opening inside said chamber.

26. A dropper according to claim 25, wherein said separate tube interior opening extends into said chamber to a distance spaced from the associated wall of said outlet tube but by an amount which is less than the amount in which said outlet tube extends into said chamber.

27. A dropper for fusion liquids particularly for connecting an infusion bag to a catheter, comprising a dropper housing defining an interior dropper chamber, an inlet connected into the top of said dropper chamber, an outlet tube extending into said chamber on a side thereof which is opposite to said inlet, and de-aeration means associated with said outlet tube for venting the interior of said chamber and having an interior opening located at one end well within said chamber to a point less than half the distance across said chamber in alignment with said inlet spaced inwardly from the side having said outlet tube, said inlet extending into said chamber to a distance less than said interior opening, said chamber being fillable with liquid upon inverting said dropper housing and filling the chamber with liquid through said outlet, said de-aeration means interior opening being spaced from said outlet within said chamber and also being spaced from its associated wall so that filling does not proceed beyond the interior opening and the remaining space in said chamber remains full of air, so that the air always remains below said inlet when the bottle is placed back in an upright position and the liquid level always remains above the interior opening of said de-aeration means, wherein said de-aeration means interior opening is formed by a separate de-aeration tube having a plurality of plate members arranged in spaced location which extend in the flow direction.

* * * * *